United States Patent
Wang et al.

(10) Patent No.: US 10,881,634 B2
(45) Date of Patent: Jan. 5, 2021

(54) METHOD FOR TREATMENT OR PREVENTION OF A DISEASE ASSOCIATED WITH A DECREASE IN BONE MASS AND METHOD OF IMPROVING BONE ARCHITECTURE AND BIO MECHANICAL STRENGTH OF BONE

(71) Applicant: HUGHES BIOTECHNOLOGY CO., LTD, Taipei (TW)

(72) Inventors: Shang-Ta Wang, Taipei (TW); Chen Hsu, Taipei (TW); Nan-Wei Su, Taipei (TW)

(73) Assignee: HUGHES BIOTECHNOLOGY CO., LTD, Taipei (TW)

( * ) Notice: Subject to any disclaimer, the term of this patent is extended or adjusted under 35 U.S.C. 154(b) by 0 days.

(21) Appl. No.: 16/190,898

(22) Filed: Nov. 14, 2018

(65) Prior Publication Data
US 2019/0175545 A1 Jun. 13, 2019

Related U.S. Application Data

(60) Provisional application No. 62/595,697, filed on Dec. 7, 2017.

(51) Int. Cl.
| | | |
|---|---|---|
| *A61K 31/352* | (2006.01) | |
| *A61P 19/10* | (2006.01) | |
| *A61K 47/52* | (2017.01) | |
| *A61P 19/08* | (2006.01) | |
| *A61P 19/00* | (2006.01) | |
| *A61K 31/661* | (2006.01) | |
| *A61P 43/00* | (2006.01) | |
| *A61K 9/00* | (2006.01) | |

(52) U.S. Cl.
CPC .......... *A61K 31/352* (2013.01); *A61K 31/661* (2013.01); *A61K 47/52* (2017.08); *A61P 19/00* (2018.01); *A61P 19/08* (2018.01); *A61P 19/10* (2018.01); *A61P 43/00* (2018.01); *A61K 9/0053* (2013.01)

(58) Field of Classification Search
CPC .... A61K 31/352; A61K 31/661; A61K 47/52; A61K 9/0053; A61P 19/08; A61P 19/00; A61P 43/00; A61P 19/10
See application file for complete search history.

(56) References Cited

U.S. PATENT DOCUMENTS

2012/0121654 A1* 5/2012 Elder, Jr. .............. A61K 9/146
424/400

OTHER PUBLICATIONS

Yamaguchi, "Anabolic effect of phosphogenistein and phosphodaidzein on bone components in rat femoral-metaphyseal tissues in vitro", J Bone Miner Metab, 2002, 20:148-155.*
Alekel et al., "The Soy Isoflavones for Reducing Bone Loss (SIRBL) Study: A 3-y randomized controlled trial in postmenopausal woman", American Journal of Clinical Nutrition, 2010; pp. 218-303.
Levis et al., "Soy Isoflavones in the Prevention of Menopausal Bone Loss and Menopausal Symptoms", Archives Internal Medicine 2011; pp. 1363-1369, vol. 171, No. 15.
Turner et al., "Genistein delivered as a once daily oral supplement had no beneficial effect on the tibia rat models for postmenopausal bone loss", Menopause, Jun. 2013; pp. 677-686.
Hsu et al., "Soy isoflavone-phosphate conjugates derived by cultivating *Bacillus subtilis* var. natto BCRC 80517 with isoflavone", Food Research International 53, 2013, pp. 487-495.
Thompson et al., "FDA Guidelines and Animal Models for Osteoporosis", Bone, Oct. 1995, pp. 125S-1333S, vol. 17, No. 4, Supplement.
Lei et al., "Ovariectomy-associated changes in bone mineral density and bone marrow haematopoiesis in rats", International Journal of Experimental Pathology, 2009, 90(5), pp. 512-519.

* cited by examiner

*Primary Examiner* — Sahar Javanmard
(74) *Attorney, Agent, or Firm* — Muncy, Geissler, Olds & Lowe, PC

(57) ABSTRACT

The present invention provides a method for treatment or prevention of a disease associated with a decrease in bone mass comprising administering to a subject in need of such treatment a composition comprising an effective amount of genistein phosphate conjugate. The present invention also provides a method of improving bone architecture and bio-mechanical strength of bone comprising administering to a subject in need of such treatment of a composition comprising an effective amount of genistein phosphate conjugate. The present invention administering to a subject in need of such treatment a composition comprising an effective amount of genistein phosphate conjugate can effectively increase the oral bioavailability so as to reduce the symptoms and the risk of complications of menopausal women, increase bone mineral content, bone density and bio-mechanical strength of bone, and slow down osteoporosis.

15 Claims, 6 Drawing Sheets

METHOD FOR TREATMENT OR PREVENTION OF A DISEASE ASSOCIATED WITH A DECREASE IN BONE MASS AND METHOD OF IMPROVING BONE ARCHITECTURE AND BIO MECHANICAL STRENGTH OF BONE

BACKGROUND OF THE INVENTION

1. Technical Field

The present invention relates to methods for treatment or prevention of a disease associated with a decrease in bone mass and methods of improving bone architecture and bio-mechanical strength of bone. More particularly, the present invention relates to methods for treatment or prevention of postmenopausal osteoporosis with genistein phosphate conjugate.

2. Description of Related Art

In a normal adult, both bone resorption and bone formation are strictly controlled, so there is only a little change in total bone mass. However, if a patient suffering from diseases associated with decrease in bone mass, balance between bone resorption and bone formation is lost and lowering bone mass and deterioration of bone tissue occur. A representative disease associated with decrease in bone mass includes osteoporosis. Previous studies revealed that the epidemiology of osteoporosis vast majority occurs in postmenopausal woman and this type of osteoporosis is called postmenopausal osteoporosis.

The therapeutic approaches for the treatment or prevention of postmenopausal osteoporosis are multiple such as a dietary supplement or an actual medicine. While the most wide-spread therapy consists in estrogen replacement therapy (ERT). ERT can effectively delay the loss of bone density, however, it also increase the risk of tumors. Concerns regarding this risk, the use of soy isoflavones are significant increasing by postmenopausal woman who seek alternatives to ERT.

Genistein, a phytoestrogen present in high concentrations in soy, possesses the most physiologically active chemical structure in soy isoflavones and is an ingredient in dietary supplements for reducing menopausal symptoms. Earlier researches considered that genistein has the potential to prevent menopausal symptoms and complications in postmenopausal woman. However, the efficacy of genistein in preventing menopause symptoms and complications, especially bone loss, in a recent, long-duration clinical trial was not significant.

Alekel et al., "The Soy Isoflavones for Reducing Bone Loss (SIRBL) Study: a 3-y randomized controlled trial in postmenopausal woman", American Journal of Clinical Nutrition 2010; 91:218-30, studied the 3-y effect of 2 doses (80 and 120 mg/d) of isoflavones extracted from soybeans (the ratio of genistein to daidzein to glycitein (aglycone form) in these extracts was 1.3:1.0:0.3) on lumbar spine and total proximal femur BMD in at-risk postmenopausal woman and the results revealed that the extracted soy isoflavones did not show a bone-sparing effect, except for a modest effect at the femoral neck. Levis et al., "Soy Isoflavones in the Prevention of Menopausal Bone Loss and Menopausal Symptoms", Archives Internal Medicine 2011; 171(15):1363-1369, studied the efficacy of the same soy isoflavone extracts in preventing bone loss and menopausal symptoms and revealed that the daily administration of 200 mg of soy isoflavones for 2 years did not prevent bone loss or menopausal symptoms. Turner et al., "Genistein delivered as a once daily oral supplement had no beneficial effect on the tibia rat models for postmenopausal bone loss", Menopause. 2013 June; 20(6): 677-686, investigated the long-term (5 months) effects of 3.2 mg/kg B.W. genistein, administered as a daily oral supplement for ovarietomized rats, but the treatment had no effect on bone mass, density or architecture in rats. As the aforesaid, the efficacy of genistein in preventing bone loss is not significant even an amount of genistein higher than that of FDA suggested (40~50 mg) was administrated. Therefore, what is needed in the art is a new composition or method for treating osteoporosis and promoting bone growth. Surprisingly, the present invention meets these and other needs.

SUMMARY OF THE INVENTION

To overcome foresaid drawback, the primary object of the present invention is to provide a method for treatment or prevention of a disease associated with a decrease in bone mass comprising administering to a subject in need of such treatment a composition comprising an effective amount of genistein phosphate conjugate.

Further, the effective amount of genistein phosphate conjugate of the composition is from about 0.5 mg/kg B.W./day to about 2.5 mg/kg B.W./day. In a preferable embodiment, the effective amount of genistein phosphate conjugate of the composition is from about 0.86 mg/kg B.W./day to about 1.73 mg/kg B.W./day. The aforesaid the effective amount of genistein phosphate conjugate of the composition is obtained according to the body-surface-area normalization method, and the range of the effective amount for human was defined by the following formula:

$$\text{Daily dosage of genistein phosphate conjugate for hunan} = \text{the effective daily dosage of genistein phosphate conjugate for rat} \times \frac{\text{human body} - \text{surface} - \text{area constant}}{\text{rat body} - \text{surface} - \text{area constant}}$$

Further, the composition is administered orally.

Further, the composition is administered at least once per day.

Further, the composition is administered from 1 to 6 times in a 24 hour period so as to give a daily dosage of genistein phosphate conjugate of from about 0.5 to about 2.5 mg/kg B.W.

Further, the composition is in a form of pills, tablets, capsules, granulates, syrups, vials or drops.

Further, the composition further comprises one or more pharmaceutically acceptable adjuvants, carriers and/or excipients.

Further, the disease is primary osteoporosis.

Further, the primary osteoporosis is osteoporosis followed by aging, postmenopausal primary osteoporosis, or osteoporosis followed by ovariectomy.

Further, the subject is mammal.

Further, the mammal is human.

Further, the human is female.

Another object of the present invention is to provide a method of improving bone architecture comprising administering to a subject in need of such treatment of a composition comprising an effective amount of genistein phosphate conjugate.

Still another object of the present invention is to provide a method of increasing bio-mechanical strength of bone comprising administering to a subject in need of such treatment of a composition comprising an effective amount of genistein phosphate conjugate.

Further, the bone is femur.

As above, comparing to the prior art, the present invention can reduce the symptoms and the risk of complications of menopausal women, increase bone mineral content, bone density and bio-mechanical strength of bone, and slow down osteoporosis through administering to a subject in need of such treatment a composition comprising an effective amount of genistein phosphate conjugate.

DETAILED DESCRIPTION OF THE EMBODIMENT OF THE INVENTION

Figure 1:
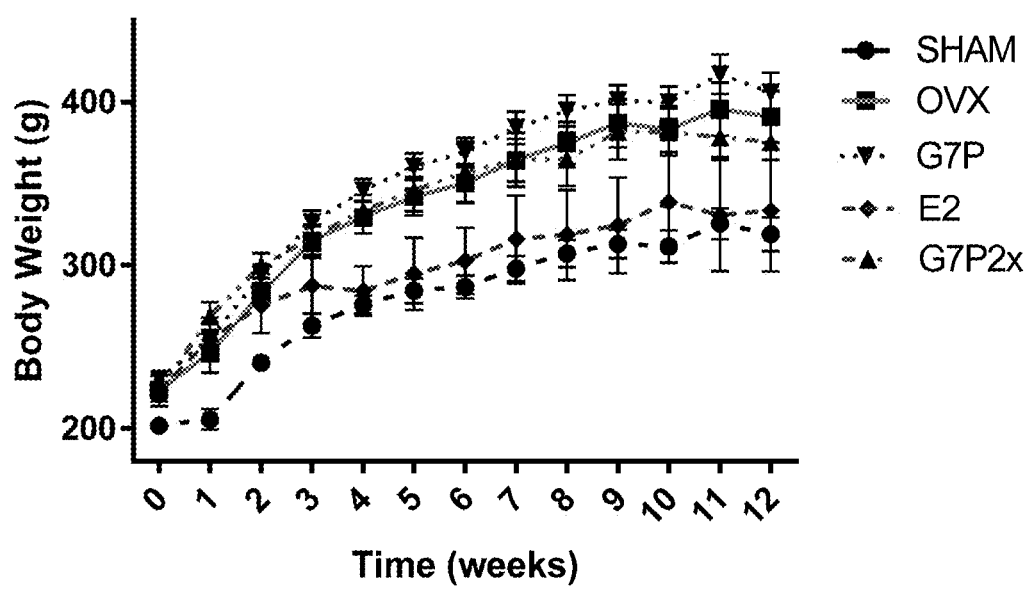
FIG. 1 is a line chart of weight gain of Example of the present invention.

A detailed description and the technical contents of the present invention are given below with reference to the accompanying drawings. Furthermore, for easier illustrating, the drawings of the present invention are not a certainly the practical proportion and are not limited to the scope of the present invention.

Unless defined otherwise, all technical and scientific terms used herein have the same meaning as commonly understood to one of ordinary skill in the art to which this disclosure belongs. As used throughout the instant application, the following terms shall have the following meanings.

The use of "or" means "and/or" unless stated otherwise. The use of "comprise" means not excluding the presence or addition of one or more other components, steps, operations, or elements to the described components, steps, operations, or elements, respectively. Similarly, "comprise," "comprises," "comprising" "include," "includes," and "including" are interchangeable and not intended to be limiting. As used herein and in the appended claims, the singular forms "a," "an," and "the" include plural referents unless the context dictates otherwise. The terms "a", "an," "the," "one or more," and "at least one," for example, can be used interchangeably herein.

The present disclosure is directed to a method for treatment or prevention of a disease associated with a decrease in bone mass comprising administering to a subject in need of such treatment a composition comprising an effective amount of genistein phosphate conjugate. Further, the present disclosure is also directed to a method of improving bone architecture comprising administering to a subject in need of such treatment of a composition comprising an effective amount of genistein phosphate conjugate. Yet further, the present disclosure is also directed to a method of increasing bio-mechanical strength of bone comprising administering to a subject in need of such treatment of a composition comprising an effective amount of genistein phosphate conjugate.

The present invention also provides a composition useful for, but not limited to, treatment and/or prevention of bone diseases such as postmenopausal osteoporosis, primary osteoporosis, or symptoms for the loss of bone density, mass, or mineral content with the additional benefit of having significantly less harmful side effect. The present invention also provides a composition useful for change of bone architecture and bone bio-mechanical strength with the additional benefit of having significantly less harmful side effect. Preferably, the primary osteoporosis is osteoporosis followed by aging, postmenopausal primary osteoporosis, or osteoporosis followed by ovariectomy.

The term "subject" refers to mammals including, but not limited to, humans, non-human primates, sheep, dogs, rodents (e.g., mouse, rat, etc.), guinea pigs, cats, rabbits, cows, horses, and non-mammals including chickens, amphibians, and reptiles, who are at risk for or have been diagnosed with a condition that causes bone loss and benefits from the methods and compositions described herein. Preferably, the subject is human, and more preferably, the human is female.

The term "treatment" as used herein is defined as maintaining or reducing the symptoms of a pre-existing condition when administered genistein phosphate conjugate compared to the same symptom in the subject prior to the administration of genistein phosphate conjugate to the subject. The term "prevention" is defined as retarding the onset of a bone disease (e.g., bone loss) in a subject.

"Genistein phosphate conjugate" (abbreviated as P-GEN in this disclosure) is a water-soluble and highly bioavailable compound. In the subject application, the genistein phosphate conjugate includes genistein 7-O-phophate (abbreviated as G7P in this disclosure, of the following formula (I)) and genistein 4'-O-phophate (abbreviated as G4'P in this disclosure, of the following formula (II). In certain embodiments, genistein phosphate conjugate was biotransformed from isoflavone by *Bacillus subtilis* var. nano BCRC 80517 (Bioresource Collection and Research Center, Taiwan), and the preparation method can be found in Hsu et al., Food Research International 53 (2013) 487-495. In certain embodiments, genistein phosphate conjugate is an effective pharmacological intervention to prevent and treatment the bone loss. In certain embodiments, genistein phosphate conjugate is used for delaying the loss of bone density, mass, and mineral content and retaining bone architecture so as to maintain the strength of bone mechanics such as maximal energy, and elastic modulus. In certain embodiments, genistein phosphate conjugate is an effective pharmacological intervention to prevent and treatment a disease associated with bone loss such as primary osteoporosis. More preferred the bone includes tibias and femurs.

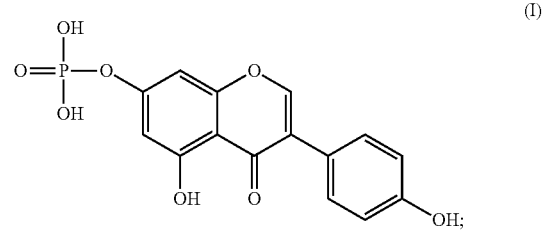

-continued

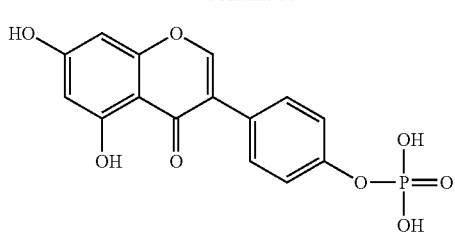

(II)

In one embodiments, the effective amount of genistein phosphate conjugate of the method of the present invention is from about 0.5 mg/kg B.W./day to about 2.5 mg/kg B.W./day, for example: 0.5 mg/kg B.W./day, 0.6 mg/kg B.W./day, 0.7 mg/kg B.W./day, 0.8 mg/kg B.W./day, 0.9 mg/kg B.W./day, 1.0 mg/kg B.W./day, 1.1 mg/kg B.W./day, 1.2 mg/kg B.W./day, 1.3 mg/kg B.W./day, 1.4 mg/kg B.W./day, 1.5 mg/kg B.W./day, 1.6 mg/kg B.W./day, 1.7 mg/kg B.W./day, 1.8 mg/kg B.W./day, 1.9 mg/kg B.W./day, 2.0 mg/kg B.W./day, 2.1 mg/kg B.W./day, 2.2 mg/kg B.W./day, 2.3 mg/kg B.W./day, 2.4 mg/kg B.W./day, or 2.5 mg/kg B.W./day. In a preferable embodiment, the effective amount of genistein phosphate conjugate of the composition is from about 0.86 mg/kg B.W./day to about 1.73 mg/kg B.W./day, for example: 0.86 mg/kg B.W./day, 0.88 mg/kg B.W./day, 0.90 mg/kg B.W./day, 0.92 mg/kg B.W./day, 0.94 mg/kg B.W./day, 0.96 mg/kg B.W./day, 0.98 mg/kg B.W./day, 1.00 mg/kg B.W./day, 1.02 mg/kg B.W./day, 1.04 mg/kg B.W./day, 1.06 mg/kg B.W./day, 1.08 mg/kg B.W./day, 1.10 mg/kg B.W./day, 1.12 mg/kg B.W./day, 1.14 mg/kg B.W./day, 1.16 mg/kg B.W./day, 1.18 mg/kg B.W./day, 1.20 mg/kg B.W./day, 1.22 mg/kg B.W./day, 1.24 mg/kg B.W./day, 1.26 mg/kg B.W./day, 1.28 mg/kg B.W./day, 1.30 mg/kg B.W./day, 1.32 mg/kg B.W./day, 1.34 mg/kg B.W./day, 1.36 mg/kg B.W./day, 1.38 mg/kg B.W./day, 1.40 mg/kg B.W./day, 1.42 mg/kg B.W./day, 1.44 mg/kg B.W./day, 1.46 mg/kg B.W./day, 1.48 mg/kg B.W./day, 1.50 mg/kg B.W./day, 1.52 mg/kg B.W./day, 1.54 mg/kg B.W./day, 1.56 mg/kg B.W./day, 1.58 mg/kg B.W./day, 1.60 mg/kg B.W./day, 1.62 mg/kg B.W./day, 1.64 mg/kg B.W./day, 1.66 mg/kg B.W./day, 1.68 mg/kg B.W./day, 1.70 mg/kg B.W./day, 1.72 mg/kg B.W./day, or 1.73 mg/kg B.W./day. In each of these aspects, administration may be via oral administration, injection including intramuscular or subcutaneous injection, transdermal or transcutaneous routes or via nasal administration. In a preferable embodiment, the administration strategy of the method of the present invention is administered orally. In a preferable embodiment, the administration strategy of the method of the present invention is administered at least once per day.

In alternative embodiments, the effective amount to be administered can be dependent on any number of variables, including without limitation, the species, breed, size, height, weight, age, overall health of the subject, the type of formulation, the mode or manner or administration, or the severity of the osteoporosis.

In one embodiment, the method of the present invention comprise one or more orally deliverable dose units comprising genistein phosphate conjugate in an amount from about 0.5 mg to about 15 mg and one or more pharmaceutically acceptable adjuvants, carriers and/or excipients.

"Excipient" as used herein includes any substance formulated alongside genistein phosphate conjugate of the composition, used as a vehicle for delivery of genistein phosphate conjugate to a subject. The excipients might aid in lubricity, flowability, disintegration, taste and may confer some form of antimicrobial function or to permit the composition to be formed into an orally deliverable dose unit having the desired shape and consistency.

"Adjuvant" as used herein refers to a substance that modifies the effect of genistein phosphate conjugate of the composition.

"Orally deliverable dose unit" as used herein refers to a dose unit of a therapeutical composition intended to be administered to the gastrointestinal tract of a subject via the mouth of the subject. In one embodiment, the dose unit can be in the form of pills, tablets, capsules, bulk powders, granulates, solutions, syrups, suspension, vials or drops. The method of the present invention can be a periodic administration of unit doses, for example: one unit dose once to multiple times a day, one with each meal, or one every four hours or other interval.

"Unit dose" as used herein refers to an amount of genistein phosphate conjugate of the composition intended for a single administration to treat a subject. In certain embodiments, the unit dose of genistein phosphate conjugate of the composition of the present invention is from about 1 mg to about 350 mg, for example: 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10.0 mg, 10.5 mg, 11.0 mg, 11.5 mg, 12.0 mg, 12.5 mg, 13.0 mg, 13.5 mg, 14.0 mg, 14.5 mg, 15.0 mg, 20 mg, 30 mg, 40 mg, 50 mg, 60 mg, 70 mg, 80 mg, 90 mg, 100 mg, 120 mg, 140 mg, 150 mg, 160 mg, 180 mg, 200 mg, 220 mg, 240 mg, 250 mg, 260 mg, 280 mg, 300 mg, 320 mg, 340 mg, or 350 mg.

In alternative embodiments, the composition of the present invention is formulated for injection into a subject because the high solubility of genistein phosphate conjugate. For injection, the composition can be formulated in aqueous solutions such as water or alcohol, or in physiologically compatible buffers such as Hanks's solution, Ringer's solution, or physiological saline buffer. The solution can contain formulatory agents such as suspending, stabilizing and/or dispersing agents. Injection formulations can also be prepared as solid form preparations which are intended to be converted, shortly before use, to liquid form preparations suitable for injection, for example, by constitution with a suitable vehicle, such as sterile water, saline solution, or alcohol, before use.

In one embodiment, the method of the present invention is to administer the composition from 1 to 6 times in a 24 hour period so as to give a daily dosage of genistein phosphate conjugate of from about 0.5 to about 2.5 mg/kg B.W. In other aspects, the composition of the present invention can be incorporated into foodstuffs, medication, or additional potable, ingestible, or edible compositions.

"Bone architecture" as used herein refers to the overall shape and geometry of bone as well as the differentiation into trabecular and cortical bone. The parameters describing architecture can be cortical thickness, bone mass, bone mineral density (BMD), trabecular bone volume, and trabecular number. "Bio-mechanical strength of bone" used herein refers to mechanical properties which are correlated with many strength criteria, for example, deformation rate during testing, density, variations in different regions of the bone. The evaluation for the degree of biomechanical test can be maximal load, maximal energy, fracture load, and Young's modulus or elastic modulus (E).

"Trabecular bone" as used herein makes up the inner layer of bone and is characterized by a lattice-like matrix network (called trabeculae) that gives it its spongy appearance. "Cortical bone" as used herein forms the cortex, or outer shell, of the bones. Cortical bone is much denser than trabecular bone and contributes about 80% of the weight of a human skeleton. However, the imbalance in bone formation and resorption (or called bone remodeling) has effects on trabecular bone (loss of connectivity) and cortical bone (cortical thinning and porosity).

The "ovariectomized rat model" is most commonly used in research on postmenopausal osteoporosis. After ovariectomy, bone resorption exceeds bone formation initially, causing bone loss. Soon thereafter, bone remodeling reaches a steady state, where resorption and formation are balanced.

The present invention is more detailed illustrated by the example embodiments as below. While example embodiments are disclosed herein, it should be understood that they are used for illustrating the present invention, not for limiting the scope of the present invention.

EXAMPLES

A. Methods (1) Experimental Animal 12-week-old female Wistar rats were used. All of experimental rats were purchased from BioLASCO Taiwan Co., Ltd. The rats were housed in the Experimental Animal Center of Taipei Medical University. The animal room was maintained under temperature of 21-24° C., relative humidity of 30-70%, and 12 hours of automatic light for alternating dark and bright. During the experimental periods, the animals were given adequate drinking water and fed with standard feed. The feeding and surgery were in accordance with the regulations of the Institutional Animal Care and Use Committee (IACUC) of Taipei Medical University.

(2) Ovariectomy and Sham Surgery

For ovariectomy rats, bilateral ovariectomy surgery was conducted at 12-week-old under anesthesia with Zoletil 50 (Tiletamine 20-40 mg/kg+Zolazepam 5-10 mg/kg) and Rompun, following the FDA Guidelines and Animal Models for Osteoporosis. For sham surgery rats, set as control group, the surgery performed surgical incision without removing the ovaries was also conducted at 12-week-old under anesthesia with Zoletil 50 (Tiletamine 20-40 mg/kg+Zolazepam 5-10 mg/kg) and Rompun. After ovariectomy surgery, 24 rats of ovariectomy group were randomly divided into 4 groups, namely, 6 rats in each group. After 2 weeks of surgery, the rats were oral administered once a day with different samples based on their groups. The rats were weighed once a week as the basis for the dose of administration for 12 weeks and the weight data were recorded. Finally, when sacrificed, the ovarian of the rats were checked to determine whether the ovariectomy surgery was successful or not, wherein the data of failed ovariectomy rat(s) would be eliminated.

(3) Experimental Periods

According to FDA guidelines and previous research, bone structures would change obviously within 12 weeks after ovariectomy surgery (FDA Guidelines and Animal Models for Osteoporosis 1995; International Journal of Experimental Pathology 2009, 90(5), 512-519).

(4) Dosage

The FDA states that 25 g of soy protein (equal to 40~50 mg of isoflavones) per day with a diet low in saturated fat and cholesterol may reduce the heart disease. Most of the dosages of soy isoflavones dietary supplements on the market are ranged in 40~60 mg/day. Therefore, 40 mg/day of G7P in human is regarded as reference dosage. According to the body-surface-area normalization method, the dosage of G7P for rats was defined by the following formula:

$$\text{Daily dosage of } G7P = \frac{\text{daily recommendation}}{\text{general human body weight}} \times$$
$$\frac{\text{human body-surface-area constant}}{\text{rat body-surface-area constant}} \times \frac{G7P \text{ MW}}{\text{genistein MW}}.$$

In one embodiment, the daily recommendation of isoflavone is 40 mg/day, general female human body weight is 60 kg, human body-surface-area constant is 37, rat body-surface-area constant is 6, G7P MW is about 350, and genistein MW is about 270 in the above formula. Applying theses values in the above formula gives the following:

$$\text{Daily dosage of } G7P = \frac{40 \text{ mg/day}}{60 \text{ kg}} \times \frac{37}{6} \times \frac{350}{270} = 5.33 \text{ mg/kg/day}$$

Therefore, the daily dosage of G7P used in this example was 5.33 mg/kg/day.

(5) Administration and Grouping

Total 30 rats were grouped into following 5 groups (i.e., "SHAM", "OVX", "G7P", "G7P2X", "E2").

a. SHAM group: sham surgery rats, set as control group, fed with sterile water by oral gavage;

b. OVX group: ovariectomized rats, set as negative control, fed with sterile water by oral gavage;

c. G7P group: ovariectomized rats, administered with 5.33 mg/kg B.W. G7P solution once per day by oral gavage, wherein the dosage was equal to 40 mg/day of the amount of soy isoflavones for adult;

d. G7P2X group: ovariectomized rats, administered with 10.66 mg/kg B.W. G7P once per day by oral gavage, wherein the dosage was equal to 80 mg/day of the amount of soy isoflavones for adult;

e. E2 group: ovariectomized rats, set as positive control, administered with 200 μg/kg B.W. 17β3 estradiol once per day by tube feeding.

(6) Bone Index Test

At week 0, 3, 6, 9 and 12 of the experimental period, in vivo micro-CT scan were conducted on the caput femoris of right leg of the rats by animal CT scanner system Sky Scan 1176 to obtain the 3D tomography image. The obtained 3D tomography images were further analyzed by software so as to obtain bone index data. The data include bone mineral density (BMD) and bone volume-to-total volume ratio (bone volume/total volume, BV/TV, %).

(7) Sacrifice and Sample Collection

After sacrificed the rats, tibias and femurs were collected for the detection of bone density and bone stress. Further, uteruses were collected and weighed after removing the surrounding fat, and the weight data was recorded.

(8) Bone Mechanics Analysis

The bio-mechanical strength of femur was measured using bio-mechanical testing instrument (RT1-TST, Royalty Tec.Ins. Ltd) after removing the soft tissue of left leg. First, the length of the femur was measured by the electronic vernier and the mid-position of the femur was set so as to be the scale standard which must be aligned when compressing the vertical physical strength of the femur by the bone stress meter. The femur was kept moist with physiological saline and fixed on a test bench for a three-point bending test. The motor revolution speed of the bone stress meter was set at 0.05 mm/sec. After the femur was compressed to fracture, the parameters of the bone mechanics analysis obtained by the test system were as follows:

a. maximal load: the force converted from the maximum weight of the record, the unit is Newton;

b. maximal energy: the area integratal under the record curve, the unit is mJ;

c. fracture load;

d. Young's modulus or elastic modulus (E).

(9) Histopathological Observation

The bone tissue of the caput femoris of right leg was fixed with para-formaldehyde after removing the soft tissue around the femur, and conducted decalcification by acid and then embedded in paraffin. The sample was sliced by a tissue microtome (slitting: circular section) to form slices having the thickness of 2 μm. The slices were adhered to a slide and stained with H&E and then the slide was fixed for bone histopathological observation.

(10) Statistical Analysis

Animal experiment data was analyzed with linear model for variance analysis and the differences between the groups were determined by Student's t-test. The data was showed in mean±standard deviation (Mean±SD).

B. Results (1) Weight Changes

The ovariectomized rat model simulated the physiological condition of menopause women which could be a platform to observe osteoporosis. Generally, organisms would gain weight if lacking of estrogen for a long time. As shown in FIG. 1, the same phenomenon was observed in all ovariectomized groups. The body weight of the ovariectomized rats increased significantly in 2 weeks after ovariectomy compared to that of the SHAM group. Furthermore, the ovariectomized rats gained weight with the experimental period, and the weight of the heaviest G7P group showed almost 400 g at week 12 after the surgery. At week 3, the rats in the E2 group began to be lighter than other ovariectomized groups, i.e. the OVX group, the G7P group, and the G7P2X group; at week 12, the weight of the E2 group were much lower than that of other ovariectomized groups. The result showed that oral administration of high dose of estrogen could reduce the weight gain caused by the deficiency of estrogen, but administration of G7P, i.e. the G7P group and the G7P2X group, did not reverse the weight gain.

(2) Uterus Development

Figure 2:
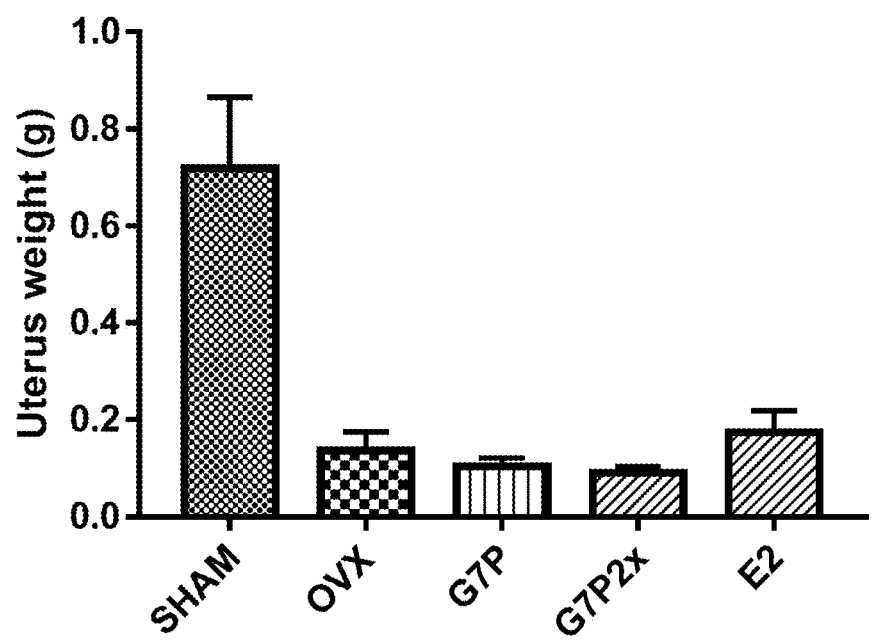
FIG. 2 is bar chart of uterus weight of Example of the present invention.

Previous studies revealed that, after removing the ovary, uterus atrophying occurs rapidly due to estrogen insufficiency. The weights of uterus of each group at the end of the experiment are showed in FIG. 2. After 12 weeks of ovariectomized surgery, the uterus weight of the ovariectomized rats was significantly lower than that of the sham surgery rats. Specifically, the uterus weight of the ovariectomized rats was almost a quarter of the normal uterus weight value, showing that the ovariectomy has been successfully done. Furthermore, all treatment in ovariectomized groups did not have any significant effect on the weight and the appearance of the atrophied uterus.

(3) Bone Mineral Density and Volume Changes

Figure 3:
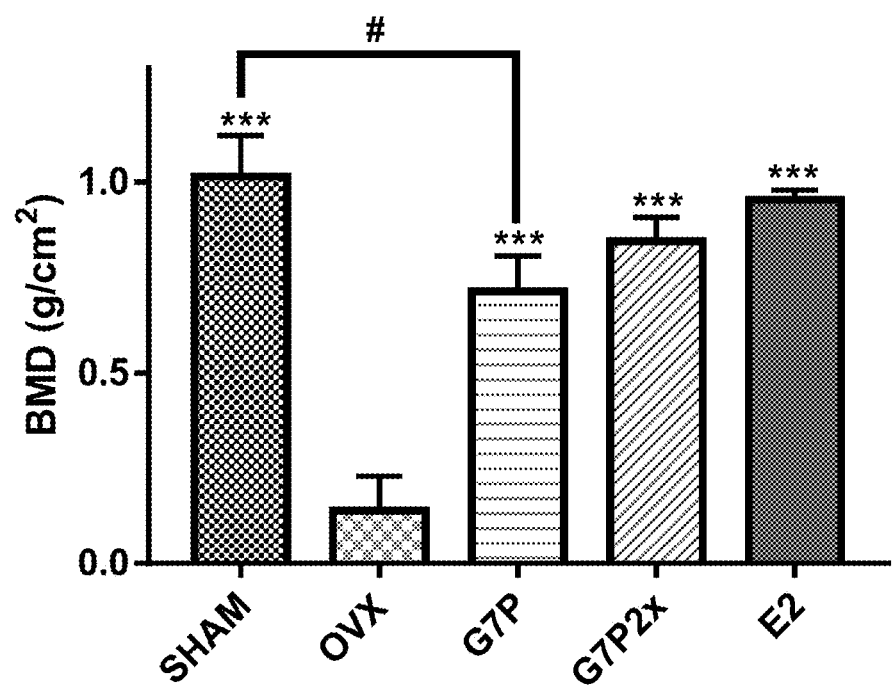
FIG. 3 is a bar chart of BMD level of Example of the present invention.

The BMD of each group at week 12 is shown in FIG. 3. The result showed that the BMD of the SHAM group increased normally with the experimental time, and the BMD reached about 1.14 g/cm² at week 12. However, the BMD of the OVX group was only about 0.03 g/cm². Obviously, all of the BMD level of the G7P group, the G7P2X group, and the E2 group were significantly higher than that of the OVX group, indicating that oral administration of G7P (the G7P group and the G7P2X group) was able to inhibit bone mineral loss and maintain BMD in the trial and generated similar effects as oral administration of 1743 estradiol of 200 μg/kg B.W. (the E2 group).

Figure 4:
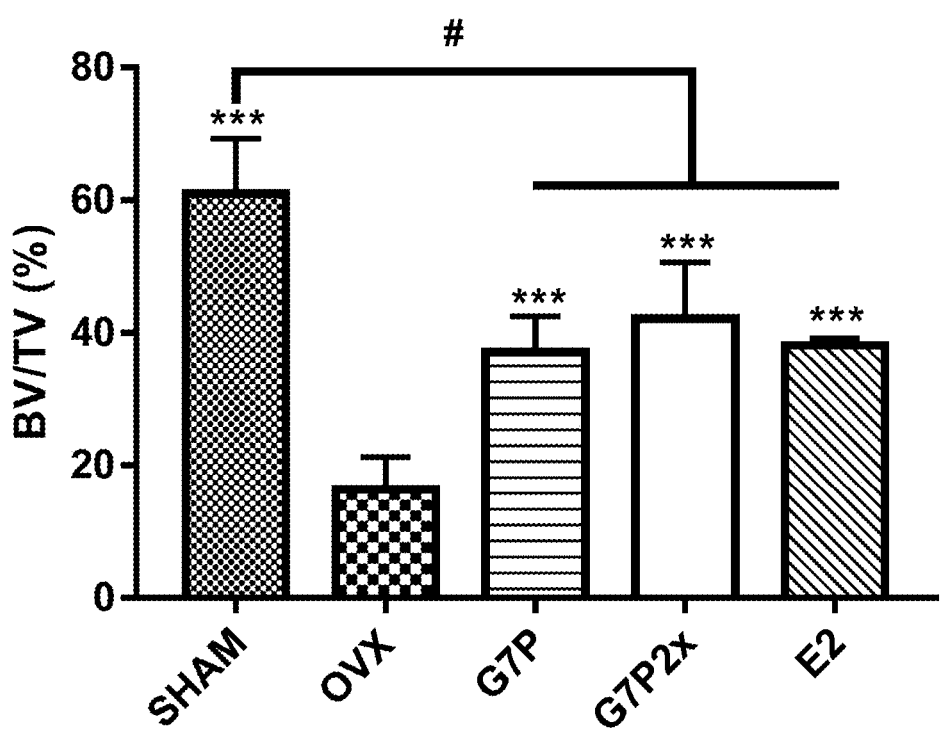
FIG. 4 is a bar chart of bone volume/total volume of Example of the present invention.

As shown in FIG. 4, the BV/TV of the OVX group was lowest in the groups. Furthermore, the BV/TV of the G7P group, the G7P2X group, and the E2 group were higher than that of the OVX group with statistical significance, wherein the BV/TV of the G7P2X group was slightly higher than that of the G7P group and the E2 group. As a result, oral administration of G7P maintained bone volume after ovariectomy and generated substantially the same effect as oral administration of estradiol.

(4) Osteoblastic Change and Trabecular Bone Development

Figure 5:
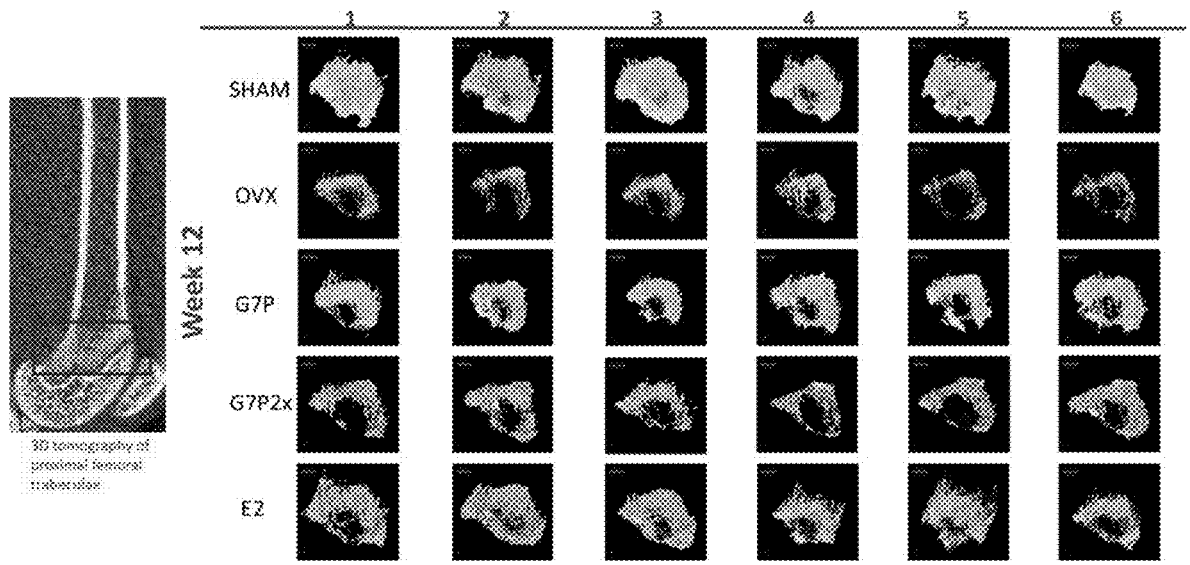
FIG. 5 is a 3D µ-CT scanning diagram of Example 1 of the present invention.

FIG. 5 shows the bone structure of the μCT 3D imaging diagram, wherein the number represents different individual experimental animal in each group. The result showed that the SHAM group had a dense distribution of trabecular structure near the caput femoris, and the range of the distribution was wider than other groups. Comparing to the SHAM group, the OVX group showed a depleted trabecular structure, especially, the meshwork of trabecular structure was almost loss at the caput femoris. In the G7P group and the G7P2X group, both of the trabecular structures were much integrated than that of the OVX group and the amount of the trabecular structures were significantly improved. Therefore, oral administration of G7P retards bone resorption and is an effectively dietary supplement for reducing bone loss. Comparing to the G7P group, a wide but loose trabecular distribution was observed in the positive control E2 group. Consequently, both oral administration of G7P and estradiol can maintain the trabecular structure of femur, but the remaining femur structures in the E2 group was significantly different from those in the G7P group in morphology.

Figure 6:
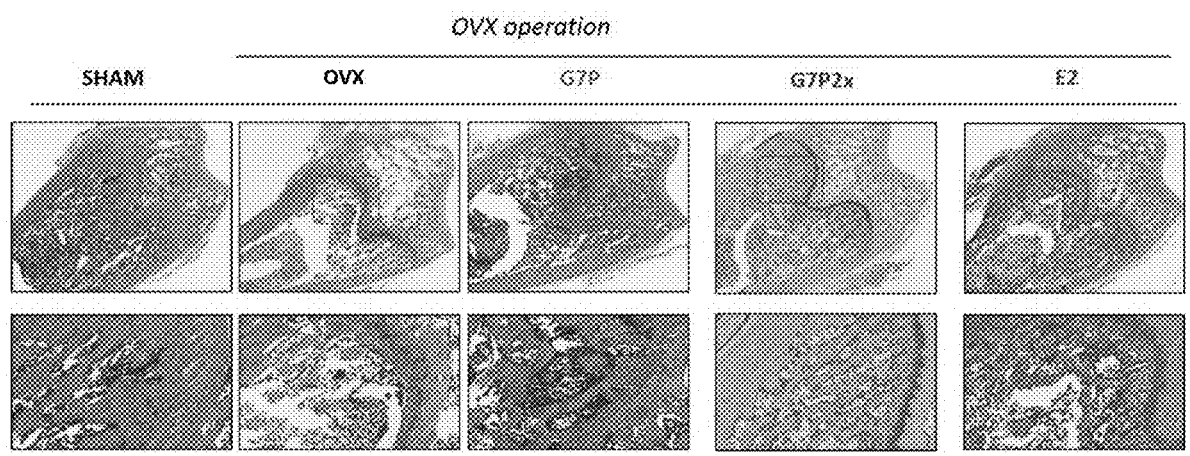
FIG. 6 is an H&E staining diagram of rat distal femur slide of Example of the present invention.

The result of histopathological observation is shown in FIG. 6. In the SHAM group, rich mineral (deep red) and dense trabecular meshwork (pink) were clearly observed in the bone tissue. There were also a certain number of osteoblasts under the growth plate, showing a strong bone formation activity in the SHAM group. Resorption in bone tissue, serious mineral loss, dispersed trabecular tissue with fragmented shape, and rare bone formation activity were observed in the OVX group. Bone mineral retention and trabecular bone density were good in the G7P group and G7P2X group, and osteoblasts can be observed around the growth plate. The retarding effects of bone loss observed in the tissue section slide in the G7P group and G7P2X group were the similar to that of the E2 group. As a result, oral administration of G7P is an effective alternative to estrogen therapy. In this embodiment, 5.33 mg/kg B.W./day of G7P retards the occurrence of osteoporosis and 10.66 mg/kg B.W./day of G7P presents better effect.

Therefore, according to the body-surface-area normalization method, the preferred dosage range of G7P for human was calculated by the following formulas:

Daily dosage of G7P for human=5.33 mg/kg B.W./day for rat×6/37=0.86 mg/kg B.W./day for human Daily dosage of G7P2X for human=10.66 mg/kg B.W./day for rat×6/37=1.73 mg/kg B.W./day for human Wherein human body-surface-area constant is 37, rat body-surface-area constant is 6 in the above formula. The obtained preferred daily dosage range of G7P for human is from about 0.86 mg/kg B.W./day to about 1.73 mg/kg B.W./day.

(5) Bone Stress

Bone loss causes a dramatic change in the mechanical strength and increases the risk of fracture or fragmentation of bone, even reducing the maximal load and the elasticity of bone. The result of the bio-mechanical strength test of the SHAM, OVX, G7P, G7P2X, and E2 groups at week 12 is shown in Table 1. The oral administration of G7P, i.e. the G7P group and the G7P2X, significantly increases the maximal energy of femur on the ovariectomized rats, and greatly increases the elastic modulus to the same level (no statistical significant difference) of the SHAM group. As a result, administration of G7P retards the occurrence of osteoporosis and has great potential to the treatment or prevention of a disease associated with a decrease in bone mass.

TABLE 1

|  | OVX | SHAM | G7P | G7P2x | E2 |
|---|---|---|---|---|---|
| Max Energy (mJ) | 61.2 ± 7.5 | 63.6 ± 2.3 | 74.4 ± 6.8* | 82.7 ± 22.8 | 76.1 ± 20.3 |
| Stiffness (N/mm) | 320.4 ± 18.0 | 343.1 ± 22.9 | 326.2 ± 43.2 | 319.1 ± 6.1 | 307.6 ± 55.1 |
| applied load (N) | 173.7 ± 14.8 | 171.7 ± 8.7 | 186.5 ± 5.9 | 197.5 ± 20.6 | 176.8 ± 12.1 |
| Strain (MPa) | 16.8 ± 3.3 | 14.1 ± 2.1 | 15.4 ± 1.9 | 18.9 ± 4.3 | 20.2 ± 7.5 |
| Elastic modulus (MPa) | 14.9 ± 2.6 | 23.3 ± 1.2** | 21.8 ± 2.6** | 22.8 ± 6.1* | 15.9.9 ± 7.4 |

$^a$ Data are mean ± SE (n = 6).
*p < 0.05 comparing with OVX group
**p < 0.01 comparing with OVX group In conclusion, through administering to a subject in need of such treatment a composition comprising an effective amount of genistein phosphate conjugate, a disease associated with a decrease in bone mass can be prevented or treated, i.e. increasing bone mineral content, bone density and bio-mechanical strength of bone, and slowing down osteoporosis.

The present invention is more detailed illustrated by the above preferable example embodiments. While example embodiments have been disclosed herein, it should be understood that other variations may be possible. Such variations are not to be regarded as a departure from the spirit and scope of example embodiments of the present application, and all such modifications as would be obvious to one skilled in the art are intended to be included within the scope of the following claims.

What is claimed is:

1. A method for treatment or alleviation of postmenopausal primary osteoporosis or osteoporosis followed by ovariectomy comprising administering to a subject in need of such treatment a composition comprising an effective amount of genistein phosphate conjugate, wherein the effective amount of genistein phosphate conjugate of the composition is from about 0.5 mg/kg B.W./day to about 2.5 mg/kg B.W./day.

2. The method for treatment or alleviation of postmenopausal primary osteoporosis or osteoporosis followed by ovariectomy of claim 1, wherein the effective amount of genistein phosphate conjugate of the composition is from about 0.86 mg/kg B.W./day to about 1.73 mg/kg B.W./day.

3. The method for treatment or alleviation of postmenopausal primary osteoporosis or osteoporosis followed by ovariectomy of claim 1, wherein the composition is administered orally.

4. The method for treatment or alleviation of postmenopausal primary osteoporosis or osteoporosis followed by ovariectomy of claim 1, wherein the composition is administered at least once per day.

5. The method for treatment or alleviation of postmenopausal primary osteoporosis or osteoporosis followed by ovariectomy of claim 4, wherein the composition is administered from 1 to 6 times in a 24 hour period so as to give a daily dosage of genistein phosphate conjugate of from about 0.5 to about 2.5 mg/kg B.W.

6. The method for treatment or alleviation of postmenopausal primary osteoporosis or osteoporosis followed by ovariectomy of claim 3, wherein the composition is in a form of pills, tablets, capsules, granulates, syrups, vials or drops.

7. The method for treatment or alleviation of postmenopausal primary osteoporosis or osteoporosis followed by ovariectomy of claim 1, wherein the composition further comprises one or more pharmaceutically acceptable adjuvants, carriers and/or excipients.

8. The method for treatment or alleviation of postmenopausal primary osteoporosis or osteoporosis followed by ovariectomy of claim 1, wherein the subject is mammal.

9. The method for treatment or alleviation of postmenopausal primary osteoporosis or osteoporosis followed by ovariectomy of claim 8, wherein the mammal is human.

10. The method for treatment or alleviation of postmenopausal primary osteoporosis or osteoporosis followed by ovariectomy of claim 8, wherein the human is female.

11. A method of improving bone architecture of a subject suffering from postmenopausal primary osteoporosis or osteoporosis followed by ovariectomy comprising administering to a subject in need of such treatment of a composition comprising an effective amount of genistein phosphate conjugate, wherein the effective amount of genistein phosphate conjugate of the composition is from about 0.5 mg/kg B.W./day to about 2.5 mg/kg B.W./day.

12. The method of improving bone architecture of a subject suffering from postmenopausal primary osteoporosis or osteoporosis followed by ovariectomy of claim 11, wherein the subject is human.

13. A method of increasing bio-mechanical strength of bone of a subject suffering from postmenopausal primary osteoporosis or osteoporosis followed by ovariectomy comprising administering to a subject in need of such treatment of a composition comprising an effective amount of genistein phosphate conjugate.

14. The method of increasing bio-mechanical strength of bone of a subject suffering from postmenopausal primary osteoporosis or osteoporosis followed by ovariectomy of claim 13, wherein the subject is human.

15. The method of increasing bio-mechanical strength of a bone of a subject suffering from postmenopausal primary osteoporosis or osteoporosis followed by ovariectomy of claim 13, wherein the bone is femur.

* * * * *